United States Patent [19]
Sherley et al.

[11] Patent Number: 5,741,646
[45] Date of Patent: Apr. 21, 1998

[54] CELL LINES AND METHODS FOR SCREENING GROWTH REGULATORY COMPOUNDS

[75] Inventors: James L. Sherley, Philadelphia; Lee B. Riley, Landsdale, both of Pa.

[73] Assignee: Fox Chase Cancer Center, Philadelphia, Pa.

[21] Appl. No.: 578,207

[22] Filed: Dec. 29, 1995

[51] Int. Cl.$^6$ .................................... C12Q 1/68
[52] U.S. Cl. .................. 435/6; 435/357; 435/375; 435/404
[58] Field of Search .............. 435/240.2, 6, 320.1, 435/357, 375, 404

[56] References Cited

PUBLICATIONS

Knudson, Seminars in Can. Biol., 3:99–106, 1992.
Cairns, Nature, 255: 197–200 1975.
Sherley, J., Biol Chem, 266: 24815–24828 1991.
Sherley et al., Cell Proliferation 28: 137–144 1995.
Sherley et al., PNAS USA, 92: 136–140 1995.
Spalholz et al., Cell 42: 183–191 1985.
Mc Neall et al., Gene, 76: 81–88 1989.
Harvey & Levine, Genes & Development 5: 2375–2385 1991.
Todaro & Green, J. Cell Biol., 17: 299–313 1963.
Pereira—Smith & Smith, Somatic Cell Genet., 7:411–421 1981.
Biscoff et al., Cancer Res., 50: 7979–7984 1990.
Morganstern & Land, NVC. Acids Res. 18: 1068 1990.
Yewdell, J. Virol., 59: 444–452 1986.
Bohmer, Meth. in Cell Biol., 33: 173–184 1990.
Shaw et al., *PNAS*, vol. 89, 1992, pp. 4495–4499.
Harvey et al., *Genes and Development*, vol. 5, 1991, pp. 2375–2385.

*Primary Examiner*—James Ketter
*Attorney, Agent, or Firm*—Dann, Dorfman, Herrell and Skillman

[57] ABSTRACT

This invention provides a novel murine cultured cell line which is derived from primary mouse embryo fibroblasts and which exhibits inducer-regulated growth kinetics. The cell line has the potential to grow either linearly or exponentially depending on exposure to an appropriate inducing agent. A corresponding cell line that does not respond to the inducing agent is also provided. The paired cell line system provides a valuable research tool for the development of therapeutic agents that target cells exhibiting deregulated growth kinetics, and also enables the identification of potential carcinogenic agents that alter stem cell renewal kinetics.

27 Claims, 3 Drawing Sheets

CELL LINES AND METHODS FOR SCREENING GROWTH REGULATORY COMPOUNDS

Pursuant to 35 U.S.C. §202 (c), it is hereby acknowledged that the U.S. Government has certain rights in the invention described herein, which was made in part with funds from the National Institutes of Health.

FIELD OF THE INVENTION

The present invention relates to the identification of anti-neoplastic drugs. Specifically, the invention provides a novel cell-based assay for screening compounds for growth regulatory activity.

BACKGROUND OF THE INVENTION

One of the major goals of cancer research is the elucidation of the mechanisms that lead to uncontrolled proliferation of neoplastic cells. A precise understanding of the molecular details of such processes will lead to the identification of new therapeutic targets and the consequent design of new diagnostic and therapeutic agents to combat human cancer. A hallmark of carcinogenesis is the loss of the tight constraints on cell division that exist in normal tissues.

Cell growth is a carefully regulated process that responds to the specific needs of the body. In a young animal, cell multiplication exceeds cell loss and the animal increases in size; in an adult, the processes of cell division and cell loss are balanced to produce a steady state. For some adult cell types, renewal is rapid: intestinal cells have a half-life of a few days before they die and are replaced; certain white blood cells are replaced as rapidly. In contrast, human red blood cells have approximately a 100-day half-life, healthy liver cells rarely die, and in adults, there is a slow loss of brain cells with little or no replacement.

The predominant form of cell division in mature animal tissues is stem cell renewal division (Knudson, Seminars in Can. Biol. 3:99–106, 1992; Cairns, Nature, 255:197–200, 1975). Unlike exponential growth, which is symmetric with respect to the divisional potential of daughter cells, renewal growth is asymmetric. Dividing stem cells in somatic tissues give rise to two daughter cells that are asymmetric in their capacity for division. One daughter cell retains the division potential of the mother cell, while the other is a non-dividing cell that differentiates to become a functional constituent of the tissue. This type of cell growth is maintained in primary cell cultures and gives rise to non-exponential, (also referred to as linear or "renewal") growth kinetics.

Tumor cells and transformed cells grown in culture have lost this tightly controlled growth regulation property and typically display exponential, rather than linear growth kinetics. Previous studies with radioactive nucleotide tracers have demonstrated that exponential growth is due to each dividing cell giving rise to two dividing daughter cells. Elucidation of the mechanisms that give rise to exponential growth would be facilitated by having available a paired cell line system that differs only in cell division kinetics.

In earlier studies, (Sherley, J. Biol. Chem. 266:24815–24828, 1991) a paired p53-inducible cell line system with conditional division kinetics was developed by stably transfecting plasmids containing a wild-type murine p53 cDNA, under the control of a temperature-inducible promoter, into murine C127 cells. In this expression system, one plasmid contained a temperature sensitive form of the bovine papilloma virus (BPV) transactivator, E2, constitutively expressed from the simian virus 40 early promoter. On a second plasmid, wild-type p53 expression was driven by a promoter controlled by the BPV long control region, the transactivation target for E2. Control cell lines were derived in parallel using a plasmid that was deleted for p53 protein coding sequences. These lines were necessary to confirm that the observed conditional division kinetics were due to changes in p53 expression and not changes in temperature alone. The parental line for these studies, C127, is an immortal, non-tumorigenic, mouse mammary epithelial cell line. At 37° C., the level of p53 expression in the inducible cells was similar to that of C127. At 32.5° C., they exhibited a 2–3-fold increase in p53 protein expression, causing growth suppression. This amount of p53 protein expression was within the physiological range observed for p53 in C127 cells (Sherley, J. Biol. Chem. 266:24815–24828, 1991).

While the above-described system demonstrates the inhibition of exponential growth and reversion to renewal growth kinetics induced by increased p53 expression, endogenous expression of p53 in the parental C127 cells places limits on the interpretation of the data. Rather than an on/off system, the foregoing paired system cannot encompass a p53-free control for the inducible cell line, due to the presence of wildtype p53 expression under non-inducing conditions. Also, the temperature sensitive phenotype requires that subsequent analyses of p53-dependent cell division kinetics be performed under non-ideal culture conditions, i.e., low temperature.

Existing cell line panels for screening anti-neoplastic compounds utilize primary tissue cells to control for effects on various tumor derived cells. Because of the myriad of differences between control cells and test cells, drug screening panels in present use are quite poor for identifying compounds that selectively affect cell division mechanisms. Ideally, screening should be carried out on identical cells that differ only in their growth kinetics. Clearly, an immortalized cell line with a tightly controlled capacity for both exponential and renewal growth would be a powerful research tool for the study of agents that target transformed cells with altered division kinetics. Such a system would facilitate the identification of compounds effective against the cellular machinery responsible for exponential, deregulated cell division but not normal cell division.

It is the object of the present invention to provide novel "conditional division" cell lines that are tightly regulated for exponential or renewal growth kinetics at the same temperature. A further object of the invention is to provide a cell culture system that will facilitate the screening and identification of agents that may be clinically relevant in the treatment of cancer. This cell line system will also find utility in the identification of compounds that have therapeutic value for other diseases that are due to changes in cell proliferative capacity, i.e., psoriasis.

SUMMARY OF THE INVENTION

In accordance with the present invention, cell lines and methods for screening growth regulatory compounds are provided. The cell lines are regulated for exponential or renewal growth kinetics. As described througout this application, the term "exponential growth kinetics" refers to a type of cell division exhibited by cells in culture and by tumor cells, wherein the cells in a population give rise to two daughter cells, both of which divide. When mathematically modeled, this type of cell division best fits an exponential equation. The term "renewal growth kinetics" refers to the type of cell division normally exhibited by mature animal tissues (e.g., stem cells and some somatic cells), wherein the cells in a population give rise to two daugter cells, only one of which retains the division potential of the mother cell. When mathematically modeled, this type of cell division best fits a linear equation. For this reason, the terms "renewal growth kinetics" and "linear growth kinetics" are used interchangeably herein. However, it is understood that cell populations rarely exhibit growth characteristics that exactly fit a mathematical equation, and variation within normal parameters for a given cell type or set of growth conditions can be expected.

According to one aspect of the invention, a mammalian cell line is provided that is devoid of functional endogenous genes encoding p53, but which is stably transfected with an exogenous DNA molecule comprising a p53 coding sequence operably linked to an inducible promoter that activates expression of the p53 coding sequence upon exposure to an inducing agent. The cell line exhibits exponential growth kinetics in the absence of the inducing agent and renewal growth kinetics upon exposure to the inducing agent.

According to another aspect of the present invention, a paired cell line system is provided for determining the effect of a substance on cell growth kinetics or for identifying, detecting or quantitating substances suspected of affecting cell growth kinetics. The paired system comprises an inducible cell line and a control cell line, both derived from the same parental cell line, which is devoid of functional endogenous genes encoding p53. The inducible cell line is stably transfected with a DNA molecule comprising a p53 coding sequence operably linked to an inducible promoter that activates expression of the p53 coding sequence upon exposure to an inducing agent. The control cell line is stably transfected with a DNA molecule comprising the inducible promoter, but lacking the p53 coding sequence. The inducible cell line exhibits exponential growth kinetics in the absence of the inducing agent and renewal growth kinetics upon exposure to the inducing agent. The control cell line exhibits exponential growth kinetics in the presence or absence of the inducing agent.

According to another aspect of the invention, a murine cell line, the "10(1)" line, is provided, having been stably transfected with an exogenous DNA molecule comprising a p53 coding sequence operably linked to a metal response element-containing (e.g., metallothionein) promoter that activates expression of the p53 coding sequence upon exposure to a metal response element inducing agent.

According to another aspect of the invention, the aforementioned 10(1) derived cell line is used as the inducible cell line in a paired cell line system for identification, detection or quantitation of substances that affect cell growth kinetics. The system also comprises a control cell line derived from 10(1) cells, which is stably transformed with an exogenous DNA molecule comprising the metal response element-containing promoter, but lacking the p53 coding sequence.

According to other aspects of the invention, methods and test kits are provided for screening potential growth regulating compounds. For instance, methods are provided for determining the effect of a substance on cell growth kinetics, which utilize an inducible cell line derived from a mammalian cell line devoid of functional endogenous genes encoding p53, stably transfected with an exogenous p53 coding sequence operably linked to an inducible promoter that activates p53 expression upon exposure to an inducing agent. The inducible cell line exhibits exponential growth kinetics in the absence of the inducing agent and renewal growth kinetics in the presence of the inducing agent. Cells are of the inducible cell line are exposed to the substance in the presence or absence of the inducing agent, and the effect of the substance on the growth kinetics of the cells is observed under inducing or non-inducing conditions.

The cell lines and methods of the present invention provide a system for the analysis of normal stem cell division without the need for primary tissue cells. They are unique in their ability to identify agents that have selective effects with respect to normal cell division versus abnormal cell division. The cell culture system of the present invention will be useful as a research tool and will facilitate the elucidation of the mechanistic action of the novel genetic and protein interactions involved in the control of somatic renewal growth. In the presence of inducing agent, the cells grow in a linear fashion (i.e., they display cell renewal growth kinetics), thus they can also be used to identify potential carcinogens that abolish normal stem cell renewal growth kinetics. They should also find broad utility in the search for diagnostic and therapeutic agents for the treatment of cancer and other proliferative diseases caused by aberrant, deregulated cell division.

BRIEF DESCRIPTIONS OF THE DRAWINGS

FIG. 1: A schematic diagram showing cell division histories that give rise to the observed linear growth kinetics of p53 inducible cells.

FIG. 2: Autoradiograph of labeled p53 protein following zinc induced expression.

FIG. 3: A graph depicting population growth kinetics of p53-induced cells. Growth data for p53-inducible line Ind-8 grown under control (−Zn, circles) or p53-inducing conditions (+90 µM Zn, squares). The mean values of duplicate data are plotted; error bars indicate the ranges of the data. Where error bars are not visible, the ranges of the data were less than the diameters of the symbols. Data were fit to either a line or an exponential. The best type fit, by least squares analysis, is shown in each case. Control data were best fit with an exponential equation, while p53-induced cell data were best fit with a linear equation.

DETAILED DESCRIPTION OF THE INVENTION

Figure 3:
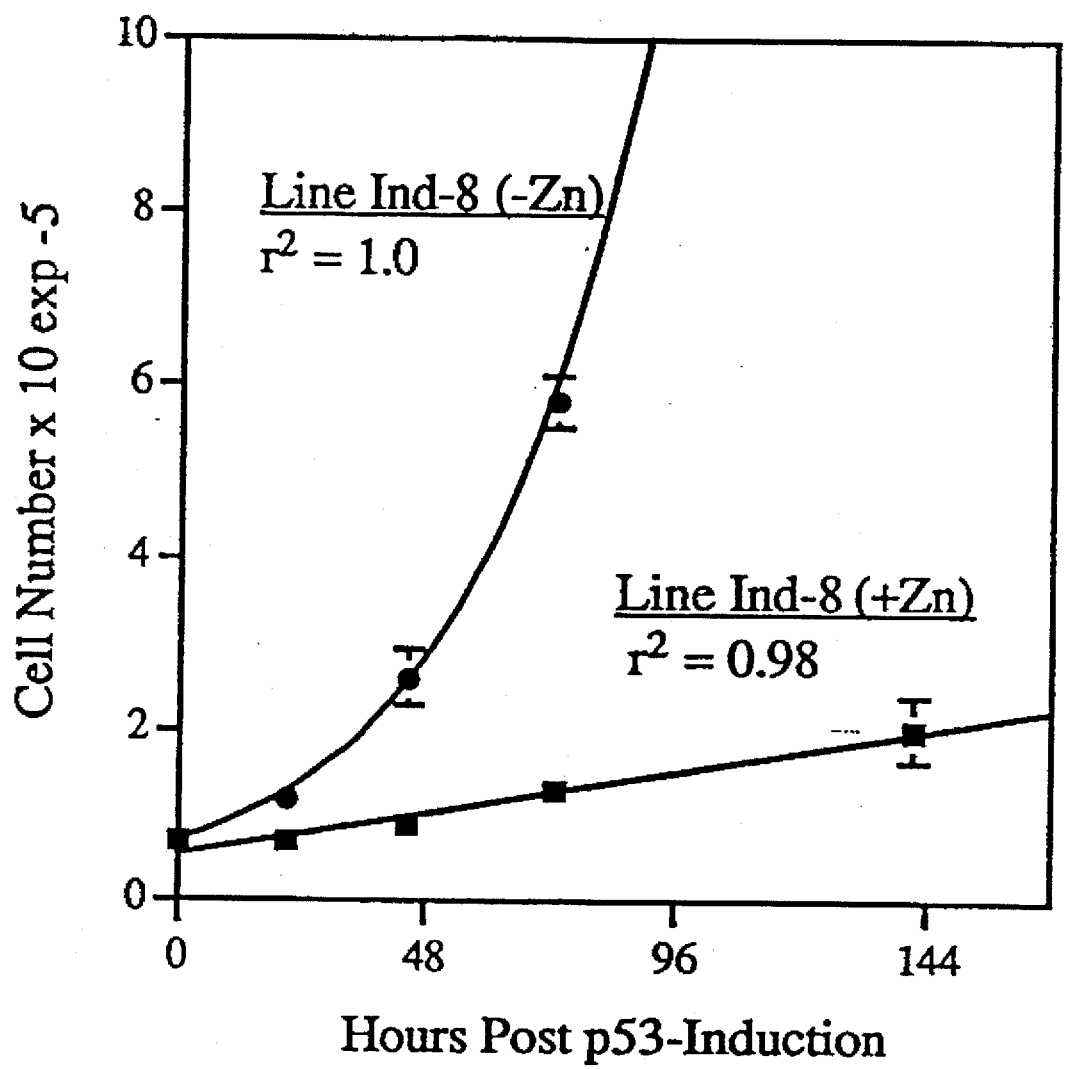

The p53 anti-oncogene is the most commonly altered genetic locus known to occur in human cancers and its product has been shown to be a negative regulator of cell growth. In accordance with the present invention, a paired cell line system useful for the screening of growth regulatory compounds is provided, which employs conditionally-induced p53 expression. In one embodiment, the p53 gene, under a human metallothionein promoter, was transfected into murine fibroblast cells devoid of p53 expression to produce a "conditional division" cell line, which is an exemplary cell line of the present invention. In parallel, control lines were derived by transfection with a similar plasmid that contained a deletion of p53 protein coding sequences. These lines are used to confirm that the observed conditional division kinetics are due to changes in p53 expression and not to zinc chloride treatment. Under non-inducing, (zinc-free) conditions, these cells divide in an exponential manner similar to transformed or tumor cells. In the presence of the inducing agent (e.g., non-toxic levels of zinc, between 40 and 90 µM $ZnCl_2$ depending on cell density), p53 expression is upregulated and the cells revert to "normal" stem cell division kinetics, also referred to in this application as linear or renewal kinetics (at lower cell density, less inducing agent is needed to achieve the same effect). Under conditions that would induce p53 expression in p53-inducible cells, growth data for control cells are best fit by an exponential equation. However, the data for p53-inducible cells under inducing conditions are best fit with a linear equation (see FIG. 3). This consistent observation reflects a biologically significant difference in the division of p53-induced cells and can be mathematically modeled (see Example 1; see also Sherley et al., Cell Proliferation 28:137–144, 1995; Sherley et al., Proc. Natl. Acad. Sci. USA 92:136–140, 1995, both incorporated herein by reference). This feature of inducer-controlled cell division will facilitate the screening of drugs that target exponentially growing (transformed cell phenotype) rather than cells growing under renewal kinetics.

I. METHODS FOR CONSTRUCTING PLASMIDS AND PRODUCING PAIRED CELL LINE SYSTEMS THAT DEMONSTRATE CONDITIONAL GROWTH KINETICS

As discussed above, the inducible system of the present invention requires the initial isolation of cells devoid of p53 expression and subsequent transfection of plasmids containing sequences encoding p53 operably linked to an inducible promoter. The detailed description set forth below describes preferred methods for making and using the cell lines and paired assay system of the present invention. Any molecular cloning, recombinant DNA or cell culture and transformation techniques not specifically described are carried out by standard methods, as generally set forth, for example, in Sambrook et al., "*DNA Cloning, A Laboratory Manual,*" Cold Spring Harbor Laboratory (1989) or Ausubel et. al., "*Current Protocols in Molecular Biology,*" John Wiley & Sons, Inc. (1995).

A. Plasmids

In a preferred embodiment of the invention, the wild-type p53 gene was excised from plasmid pLCRcala (Sherley, 1991, supra) by digestion with restriction enzymes. Plasmid pLCRcala contains the wild type murine p53 cDNA inserted downstream of the previously described LCR-SV40 hybrid promoter (Spalholz et al., Cell 42:183–191, 1985). The 1492 base-pair fragment containing the wildtype p53 cDNA sequence was excised from pLCRcala, gel purified and inserted into the HindIII site of the vector pM2.6 (McNeall et al., Gene 76:81–88, 1989). This vector contains multiple copies of a metal responsive element (MRE) within 150 bp of the transcriptional start site. The MREs also confer metal inducibility on heterologous promoters, with the degree of induction increasing with the number of elements present. This vector has very low basal level expression and an increased differential between expression in the induced and uninduced state. For selection purposes, plasmid pJ4Ω.puro was co-transfected with the p53 containing construct. Expression of this plasmid confers resistance to the antibiotic puromycin and facilitates stable cloning of transfected cells. Control cell lines were constructed by co-transfection of pM2.6, containing no p53 gene insert and pJ4Ω.puro.

In alternative embodiments, additional vectors may be constructed based on p53 sequences derived from other species, such as humans. Such sequences are known and thus it would be apparent to those skilled in the art to substitute such sequences in the above-mentioned vectors. Other inducible enhancer/promoter element sequences are available and could be substituted for the metallothionein promoter. These include, but are not limited to, the glucocorticoid response elements, cAMP response elements, IPTG response elements, tetracycline response elements, interferon response elements, erythropoietin response elements, recombination-dependent elements and heat shock promoter elements. As with sequences encoding p53, the above mentioned promoter sequences are known and insertion of any of the above into a suitable vector to control p53 expression may be accomplished according to standard methods. As used herein, the term "operably linked" means that the p53 coding sequence, promoter and suitable vector are arranged and constructed in the appropriate orientation and frame, according to standard methods, so as to be capable of inducible expression of p53 in the transfected cells.

It will also be appreciated that plasmids encoding other antibiotic resistance genes, such as neomycin or hygromycin may be used to facilitate selection of transfected cells. Selection of positive clones may also be performed by transfection of genes conferring resistance to other compounds. For example, methotrexate or histidine may be utilized for selection purposes in the present invention.

B. Cell Lines

In a preferred embodiment, cell lines of the invention are derived from the "10(1)" cell line, which is an immortalized murine fibroblast line selected for a homozygous deletion of the p53 gene (Harvey and Levine, Genes and Development 5:2375–2385, 1991). To derive the 10(1) cell line, primary cultures were established according to the methods set forth by Todaro and Green, J. Cell Biol. 17:299–313 (1963), for spontaneous immortalization of primary murine fibroblasts on a 3T3 schedule.

In alternative embodiments, cells other than murine fibroblasts are utilized. Immortalization of human cells on a 3T3 schedule rarely occurs (Pereira-Smith and Smith, Somatic Cell Genet. 7:411–421 1981). However, as p53 is the most commonly altered genetic locus known to occur in human cancers, tumor-derived cells containing mutations or deletions of p53 are common, and can be identified using standard screening techniques. In addition, non-tumorigenic cell lines containing p53 mutations have been derived from patients that have a heterozygous germline defect in one p53 gene allele (Bischoff et al., Cancer Res. 50:7979–7984, 1990). Southern hybridization may be used to determine the extent of the deletions and/or mutations in the gene encoding p53.

To achieve stable introduction of an exogenous p53 gene, plasmid DNA must first be introduced into the host cells. This may be accomplished according to numerous methods known in the art, including, but not limited to: (1) calcium phosphate transfection; (2) transfection with DEAE-dextran; (3) electroporation; and (4) liposome-mediated transfection. For general protocols, see, e.g., chapter 9 in *Current Protocols in Molecular Biology,* Ausubel et al. (editors), John Wiley & Sons, Inc. 1987–1995. For stable transfer of genes into mammalian cells, the calcium phosphate precipitation transfection method is preferred in the instant invention.

In accordance with the present invention, cell lines can be generated by co-transfection of plasmids encoding a p53 gene under the regulatory control of an inducible promoter (e.g., the metallothionien promoter) and a plasmid encoding a gene that confers resistance to an antibiotic (e.g., puromycin).

Stable transfectants are selected by the ability of an individual cell colony to grow in the presence of the antibiotic by virtue of the resistance gene carried on the transfecting plasmid DNA and incorporated into the genome of the cell.

Detection and quantitation of expression of p53 in stably-transfected cell lines of the invention can be accomplished by a variety of known assays. For instance, cells stably transfected with p53 are grown in the appropriate medium for a defined period of time and extracts are prepared. The amount of induced p53 can then be measured with an ELISA assay. Alternatively, p53 mRNA levels may be detected with Northern blotting and p53 protein levels by immunoprecipitation or Western blotting (see Example 1).

Using the assays described above, stably transfected cell lines can be selected which possess optimum characteristics for use in cell-based assays of potential growth regulatory compounds.

C. Exemplary Cell Lines

Exemplary cell lines of the present invention are the 10(1) derivatives, referred to as Ind-4 and Ind-8, and their paired exponentially growing control lines, referred to as Con-2 and Con-3. Con lines contain the pM2.6 vector without p53 encoding sequences. Ind-4 and Ind-8 were created by transfecting p53 under an inducible metallothionein-type promoter in the presence of a plasmid containing a selectable marker gene (see Example 1). As mentioned above, these cell lines grow exponentially in the absence of zinc and substantially linearly in the presence of zinc.

II. USES OF CELL LINES FOR CELL BASED ASSAYS OF POTENTIAL GROWTH REGULATORY COMPOUNDS

The "conditional division" paired cell line system of the present invention may be used as a unique screening tool for anti-cancer compounds. Existing cell line panels for this purpose use primary tissue cells (e.g., bone marrow cells) to control for effects of test compounds on various tumor-derived cells. Because of the myriad of differences between these control cells and test cells, screening cell panels currently used are quite poor for identifying compounds that selectively affect cell division mechanisms. The conditional division cell lines of the present invention allow the comparison of screens of the same cells in either a cancer-like growth state or in a normal growth state. Such screens should reveal highly selective compounds that interfere specifically with cancer cell division but not normal cell division.

The cell lines of the invention can be conveniently packaged into test kits for use in identification, detection or quantitation of cell growth-regulating substances. Such kits are commonly used by those skilled in the art, and normally contain aliquots of the cell lines and instructions for their culture and use in accordance with the present invention. The kits optionally may contain one or more inducing agents, culture media or other reagents normally used in the assays described above.

The following examples are provided to describe the invention in greater detail. The examples are intended to illustrate, not to limit, the invention.

EXAMPLE 1

Production of a Zinc-Inducible Conditional Division Cell Line Pair

Materials and Methods:

The immortalized "10(1)" cell line, derived from murine fibroblasts isolated from 14-day BALB/c embryos (Harvey and Levine, 1991, supra), was used to make the cell lines described in this example. The 10(1) cell line contains a homozygous deletion for the p53 gene.

Plasmid Construction. The wild type p53 gene was excised from plasmid pLCRcala (Sherley, 1991, supra) by digestion with the restriction enzymes BamHI and TfiI. The fragment ends were filled in with the Klenow fragment of DNA Polymerase I and ligated to HindIII linkers. Following digestion with HindIII, the 1492 basepair fragment containing the wildtype p53 gene cDNA sequence was gel purified and inserted into the HindIII site of the vector pM2.6 (McNeall et al., 1989, supra) such that its expression was controlled by the metallothionein promoter of the vector. This plasmid was called pHMT.wt.

Derivation of p53 inducible cell lines. Five μg of either plasmid pHMT.wt or plasmid pM2.6 was co-transfected by the $CaPO_4$ procedure into $1\times10^6$ 10(1) cells with 2 μg of a plasmid conferring resistance to the antibiotic puromycin (pJ4Ω.puro; Morgenstern and Land, Nucleic Acids Research 18:1068, 1990). At the time of antibiotic selection, the transfected cells were diluted 10-fold and replated in parallel in selective medium with no other addition; with the addition of 60 μM ZnCl; or with the addition of both 60 μM ZnCl and 400 μM xanthosine to score for a Zn-dependent growth arrest that was prevented by xanthosine. It has been shown in previous work that xanthosine prevents p53-induced linear division kinetics (Sherley et al., 1991, supra). These criteria being met, clonal control cell lines (Con-2 and Con-3) and p53 inducible lines (Ind-4 and Ind-8) were derived with colonies from the transfections that received no media additions and included plasmid pM2.6 and plasmid pHMT.wt, respectively.

Growth Curve Analysis. For growth curve analyses, cells were grown to one-quarter confluency at 37° C. in the absence of zinc and replenished with fresh growth medium (DMEM, 10% dialyzed fetal bovine serum, 5 μg/ml puromycin). Sixteen hours later, the cells were replated at the required density into 25 $cm^2$ flasks in the same medium. Sixteen to 24 hours later, the media was replace with fresh medium with and without zinc chloride. Cell counts were performed using a Model ZM Coulter Counter. For microcolony analysis 200–300 cells per 75 $cm^2$ flask were plated. This sparse plating allowed the counting of cell groups starting with single cells, as on average only one or two cell groups were present per 40× microscope field.

Cell labeling and Immunoprecipitation. p53 transfected 10(1) cells were grown under standard conditions for 48 hours in medium containing 0, 60, 75 or 90 μM $ZnCl_2$. Cells were metabolically labeled for 1 hour in methionine-free DMEM, 10% dialyzed fetal bovine serum containing 50–100 μCi/ml L-[$^{35}$S]methionine. Soluble extracts were prepared by direct addition of extraction buffer to flasks of labeled cells after briefly rinsing with ice-cold phosphate buffered saline. Immunoprecipitations were performed using 200 μl of supernatants from saturated cultures of hybridoma cell lines which produce specific anti-p53 monoclonal antibodies (Yewdell, J.Virol. 59:444:452, 1986). In all experiments, comparisons were made based on immunoprecipitations with extract volumes containing equal quantities of trichloroacetic acid-precipitable radioactivity. Autoradiograms were quantitated by scanning densitometry with a Pharmacia LKB UltroScan XL laser densitometer.

Figure 1:
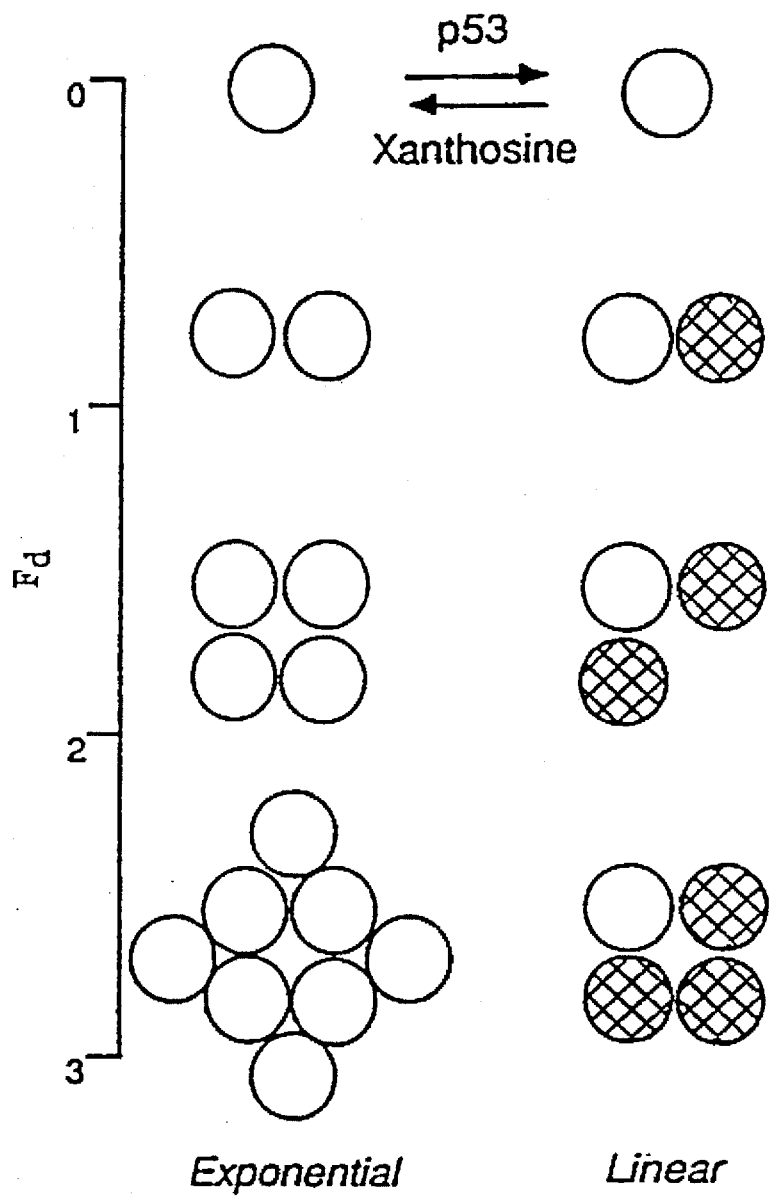
Figure 2:
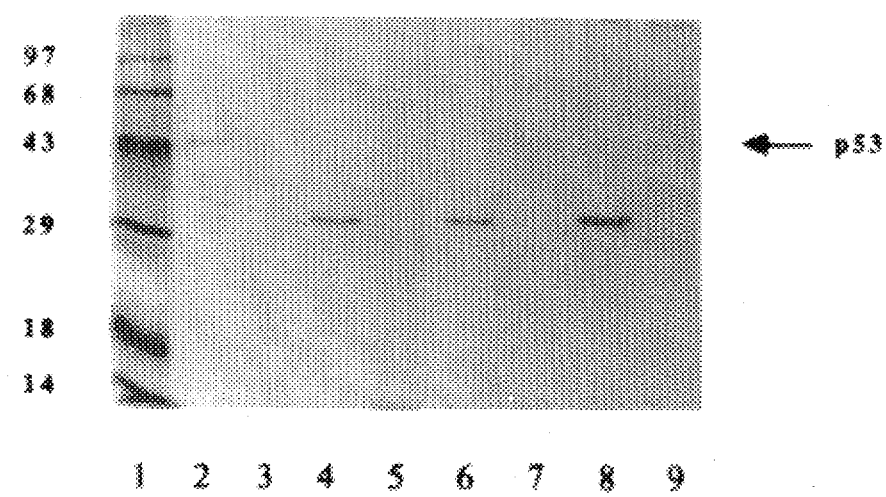

Results:

Characterization of p53 expression in the presence and absence of $ZnCl_2$. Following transfection and stable cloning of puromycin resistant, p53 containing cells, induction of p53 in the presence of zinc was assessed with metabolic labeling and immunoprecipitation. The data are shown in FIG. 2. In the absence of zinc, transfected cells contain undetectable levels of p53. In the presence of 75 μM ZnCl$_2$, p53 expression is maximally induced.

Characterization of p53 phenotype in Inducible Cell Lines. After stable cloning, transfected cells were exposed to ZnCl$_2$ to induce p53 expression and effects on cell growth were assessed. A p53 induction phenotype was readily apparent upon examination of the growth properties of the induced cells relative to the control cells not exposed to zinc. Such data are presented in FIG. 3. As can be seen in the graph, the presence of zinc chloride suppresses growth (as measured by an increase the doubling time) of the pHMT.wt transfected cells by a factor of 3.

Two methods were used to confirm the stem cell division kinetics of the zinc-dependent p53 inducible lines. The first was a mathematical procedure originally developed to quantify the division kinetics of temperature-dependent p53-inducible lines (Sherley et al., Cell Prolif., 1995, supra). The second was a bromodeoxyuridine-Hoechst dye fluorescence quench procedure used to visualize and quantify the daughter cell products of p53-induced stem cell division (Bohmer, Meth. in Cell Biol. 33: 173–184, 1990). Data from the mathematical method are presented in Table I. This method estimates the division frequency of new daughter cells, termed $F_d$ (Sherley et al., Cell Prolif., 1995, supra). $F_d$ is an indicator of cell division pattern that can be applied to population growth data. Values near 1.0 indicate symmetric renewal division (i.e., exponential growth kinetics); values near 0.5 indicate asymmetric cell renewal division (i.e., linear or renewal growth kinetics). In the absence of zinc, the calculated $F_d$ values for both p53-inducible lines and control lines approximate the ideal value for exponential division, 1.0. However, upon p53 induction by the addition of zinc, the p53 inducible cell lines, Ind-4 and Ind-8 exhibit $F_d$ values that approach the ideal value for linear renewal division, 0.5. This effect is not observed for control lines in the presence of zinc, indicating that the change in division kinetics is due to p53 protein expression and not zinc per se.

Linear renewal division is characterized by the production of a dividing daughter cell and a non-dividing daughter cell for each cell division event. Thus, p53-induced cell populations that grow with renewal kinetics are predicted to contain both cycling dividing cells and non-cycling non-dividing cells. The presence of these two distinct subpopulations of cell was demonstrated by the bromodeoxyuridine-Hoechst dye fluorescence quench procedure of Bohmer (Bohmer, 1990, supra). In this method, non-cycling cells are visualized as dim cells when stained with Hoechst dye, because such cells incorporate bromodeoxyuridine which quenches the UV-fluorescence of the dye. On the other hand, non-cycling, and therefore non-dividing cells do not incorporate bromodeoxyuridine and appear bright after staining with Hoechst dye. In this procedure, when grown in the presence of zinc, p53-inducible lines Ind-4 and Ind-8 exhibited both dim cells and bright cells in proportions consistent with stem cell renewal division. However, when grown in the absence of zinc, these cells were uniformly dim. Control cells were uniformly dim when grown in the presence or absence of zinc.

It was concluded that expression of the wild-type p53 protein within its physiological range in immortalized cells Ind-4 and Ind-8 induces a cell division program like that of renewing stem cells. By contrast, non-induced cells (having no endogenous p53) exhibit clearly exponential growth kinetics. This property has also been observed for another independently derived p53 inducible cell line derived from C127 cells (Sherley, 1991, supra). However, in that system, induction of p53 was based on a temperature sensitive transcriptional activator, so growth kinetics of exponential versus linearly growing cells were measured at two different temperatures. Temperature based induction did not allow for graded p53 expression as in the case of zinc inducible cells. Moreover, non-induced cells of the previously-described system expressed a wild-type p53, so a true non-expressing control was unavailable.

Cell growth rates and $F_d$ values of Ind-4 cells following treatment with zinc are shown in Table I.

TABLE I

| [ZnCl$_2$] | Growth Rate (Doubling Time) | Growth Kinetics (Estimated $F_d$) |
|---|---|---|
| 0 | 19–22 hours* | 0.99–1.0 |
| 60 μM | 18–23 hours | 0.98–1.0 |
| 75 μM | 31–44 hours | 0.63–0.67 |
| 85–90 μM | 75–151 hours | 0.51 |

*Same as control cells. Control line doubling times are unaffected by ZnCl$_2$ up to 75–80 μM. At 85 and 90 μM zinc the doubling time of control lines increased to 30 and 38 hours respectively. For the entire range of ZnCl$_2$ concentrations analyzed, $F_d$ for controls ranged from 0.95 to 1.0.

Discussion:

These studies demonstrate that expression of p53 in cells devoid of p53 has profound consequences for the future growth of a cell. Induction of p53 expression in exponentially growing cells to a level similar to that seen in cells rendered quiescent by serum deprivation is shown to induce a new quiescent state. This p53-induced state is unique in that it represents a type of "physiologic quiescence" in culture, i.e. quiescence in the presence of serum growth factors. This novel culture state promises to be more similar to the state of nondividing cells in vivo and provides a valuable research tool in the study of the regulation of cell growth. The culture system described herein allows for testing of compounds that not only potentially inhibit neoplastic growth and thus have clinical value for the treatment of cancer, but also facilitates the identification of compounds that may induce neoplastic growth (by abolishing the stem cell renewal kinetics manifested by the p53 induced cells) thereby identifying potential carcinogenic agents.

EXAMPLE 2

Phenotypic Reversal of p53-Induced Linear Growth Kinetics by Hypoxanthine

As an illustrative example of how the conditional cell lines can be used to investigate the mechanism of action of agents that control cell division, the following example is provided. Hypoxanthine and xanthosine are well-defined salvage precursors for purine nucleotide biosynthesis. In the studies that defined the properties of the described p53-inducible cell lines, these compounds have been used as probes to the underlying biochemical mechanisms. They have very different effects on the division properties of cells that depend on p53 expression status. In the case of p53-induced cells, the addition of hypoxanthine or xanthosine to the growth medium led to a decrease in doubling time division kinetics (Sherley et al., 1991, supra; Sherley et al., 1995, supra). Under similar growth conditions, the exponential growth of control cells or p53 inducible cells grown under non-inducing conditions was completely unaffected by the addition of these compounds. From these findings, it is evident that, in a general screen for compounds that selectively affect the division of cells depending on their p53-status or cell division pattern, hypoxanthine and xanthosine would be identified. In a similar fashion, the cell lines can be used to identify other compounds that selectively modify the division kinetics of cells depending on their pattern of cell division and/or p53 expression status.

The description and examples set forth above describes preferred embodiment of the invention. Other embodiments may be apparent to those skilled in the art. Therefore, the invention is not limited to the particular embodiments described, but may be capable of modification or variation without departing from the spirit of the invention, the full scope of which is delineated by the appended claims.

What is claimed is:

1. A murine cell line devoid of functional endogenous genes encoding p53, the cell line being stably transformed with an exogenous DNA molecule comprising a p53 coding sequence operably linked to an inducible promoter that activates expression of the p53 coding sequence upon exposure to an inducing agent, the cell line exhibiting exponential growth kinetics in the absence of the inducing agent and renewal growth kinetics upon exposure to the inducing agent.

2. The cell line of claim 1, which is a murine embryo fibroblast cell line.

3. The cell line of claim 2, derived from a murine fibroblast 10(1) cell line.

4. The cell line of claim 1, wherein the p53 coding sequence is a mouse coding sequence.

5. The cell line of claim 1, wherein the inducible promoter comprises at least one metal response element.

6. The cell line of claim 5, wherein the inducing agent is zinc.

7. A test kit for determining the effect of a substance on cell growth kinetics, the kit comprising and aliquot of the cell line of claim 1, and directions for using the cell line.

8. The test kit of claim 7, which further comprises an aliquot of the inducing agent.

9. A murine 10(1) cell line, stably transfected with an exogenous DNA molecule comprising a p53 coding sequence operably linked to a metal response element-containing promoter that activates expression of the p53 coding sequence upon exposure to a metal response element inducing agent, the cell line exhibiting exponential growth kinetics in the absence of the inducing agent and renewal growth kinetics upon exposure to the inducing agent.

10. The cell line of claim 9, stably transformed by co-transfection with plasmids pHMT.wt and pJ4Ω.puro.

11. The cell line of claim 10, selected from the group consisting of Ind-4 and Ind-8.

12. A paired cell line system for determining the effect of a substance on cell growth kinetics, the system comprising an inducible cell line and a control cell line, both the lines derived from a mammalian parent cell line devoid of functional endogenous genes encoding p53;

a) the inducible cell line being stably transfected with an exogenous DNA molecule comprising a p53 coding sequence operably linked to an inducible promoter that activates expression of the p53 coding sequence upon exposure to an inducing agent, the inducible cell line exhibiting exponential growth kinetics in the absence of the inducing agent and renewal growth kinetics upon exposure to the inducing agent;

b) the control cell line being stably transfected with an exogenous DNA molecule comprising the inducible promoter but lacking the p53 coding sequence, the control cell line exhibiting exponential growth kinetics in the presence or absence of the inducing agent.

13. The system of claim 11, wherein the parental cell line is a murine cell line.

14. The system of claim 13, wherein the parental cell line is a murine embryo fibroblast cell line.

15. The system of claim 14, wherein the parental cell line is derived from a murine fibroblast 10(1) cell line.

16. The system of claim 12, wherein the p53 coding sequence is a mouse coding sequence.

17. The system of claim 12, wherein the inducible promoter comprises at least one metal response element.

18. The system of claim 17, wherein the inducing agent is zinc.

19. A test kit for determining the effect of a substance on cell growth kinetics, the kit comprising:

a) an aliquot each of the inducible cell line and the control cell line of claim 12; and b) directions for using the cell lines.

20. The test kit of claim 19, which further comprises an aliquot of the inducing agent.

21. A paired cell line system for determining the effect of a substance on cell growth kinetics, the system comprising an inducible cell line and a control cell line, both lines derived from a murine 10(1) cell line, the inducible cell line being stably transfected with an exogenous DNA molecule comprising a p53 coding sequence operably linked to a metal response element-containing promoter that activates expression of the p53 coding sequence upon exposure to a metal response element inducing agent, the control cell line being stably transfected an exogenous DNA molecule comprising the metal response element-containing promoter but lacking the p53 coding sequence.

22. The system of claim 21, wherein the inducible cell line is stably transformed by co-transfection with plasmids pHMT.wt and pJ4Ω.puro, and the control cell line is stably transfected by co-transfection with plasmids pM2.6 and pJ4Ω.puro.

23. The system of claim 22, wherein the inducible cell line is selected from the group consisting of Ind-4 and Ind-8, and the control cell line is selected from the group consisting of Con-2 and Con-3.

24. A method for determining the effect of a substance on cell growth kinetics, the method comprising:

a) providing an inducible cell line derived from a mammalian parent cell line devoid of functional endogenous genes encoding p53, the inducible cell line being stably transfected with an exogenous DNA molecule comprising a p53 coding sequence operably linked to an inducible promoter that activates expression of the p53 coding sequence upon exposure to an inducing agent, the inducible cell line exhibiting exponential growth kinetics in the absence of the inducing agent and renewal growth kinetics upon exposure to the inducing agent;

b) exposing cells of the inducible cell line to the substance; and c) observing whether the exposure of the cells to the substance alters the growth kinetics of the cells, the alteration being indicative of the effect of the substance on cell growth kinetics.

25. The method of claim 24, wherein the cells are exposed to the substance in the absence of the inducing agent.

26. The method of claim 24, wherein the cells are exposed to the substance in the presence of the inducing agent.

27. The method of claim 24, which further comprises:

d) providing a control cell line derived the mammalian parent cell line devoid of functional endogenous genes encoding p53, the control cell line being stably transfected with an exogenous DNA molecule comprising said inducible promoter but lacking said p53 coding sequence, the control cell line exhibiting exponential growth kinetics in the presence or absence of the inducing agent;

b) exposing cells of the control cell line to the substance; and c) comparing the effect of the substance on the growth kinetics of the control cell line with the effect of the substance on the growth kinetics of the inducible cell line.

* * * * *